United States Patent [19]

Parnoff et al.

[11] Patent Number: 4,679,573
[45] Date of Patent: Jul. 14, 1987

[54] ADAPTOR ASSEMBLY FOR AIRWAY TUBE

[75] Inventors: George K. Parnoff, Walnut Creek; Steven L. Sultan, Berkeley, both of Calif.

[73] Assignee: Andros Analyzers Incorporated, Berkeley, Calif.

[21] Appl. No.: 895,056

[22] Filed: Aug. 11, 1986

Related U.S. Application Data

[63] Continuation of Ser. No. 670,308, Nov. 8, 1984, abandoned.

[51] Int. Cl.$^4$ ................................................. A61B 5/08
[52] U.S. Cl. ...................................... 128/716; 128/719
[58] Field of Search ............... 128/716, 717, 719, 730, 128/204.22, 205.12, 205.29; 422/83

[56] References Cited

U.S. PATENT DOCUMENTS

| | | | |
|---|---|---|---|
| 2,577,606 | 12/1951 | Conley | 128/205.29 |
| 3,815,754 | 6/1974 | Rosenberg | 128/205.29 |
| 3,927,670 | 12/1975 | Turney et al. | 128/719 |
| 4,122,842 | 10/1978 | Pikul | 128/725 |
| 4,159,954 | 7/1979 | Gangemi | 128/205.29 |
| 4,386,948 | 7/1983 | Choksi et al. | 128/205.29 |
| 4,423,739 | 1/1984 | Passaro et al. | 128/719 |
| 4,446,869 | 5/1984 | Knodle | 128/719 |
| 4,456,014 | 6/1984 | Buck et al. | 128/719 |

Primary Examiner—Lee S. Cohen
Assistant Examiner—Ruth S. Smith
Attorney, Agent, or Firm—Fitch, Even, Tabin & Flannery

[57] ABSTRACT

An adaptor assembly is described for sampling gas in an airway tube attached to a patient. The adaptor assembly employs a filter arrangement in a subassembly which extends transversely of the axis of the patient's airway and maximizes the ratio of the effective filter area to the dead volume added by the adaptor assembly to the sampling system.

8 Claims, 5 Drawing Figures

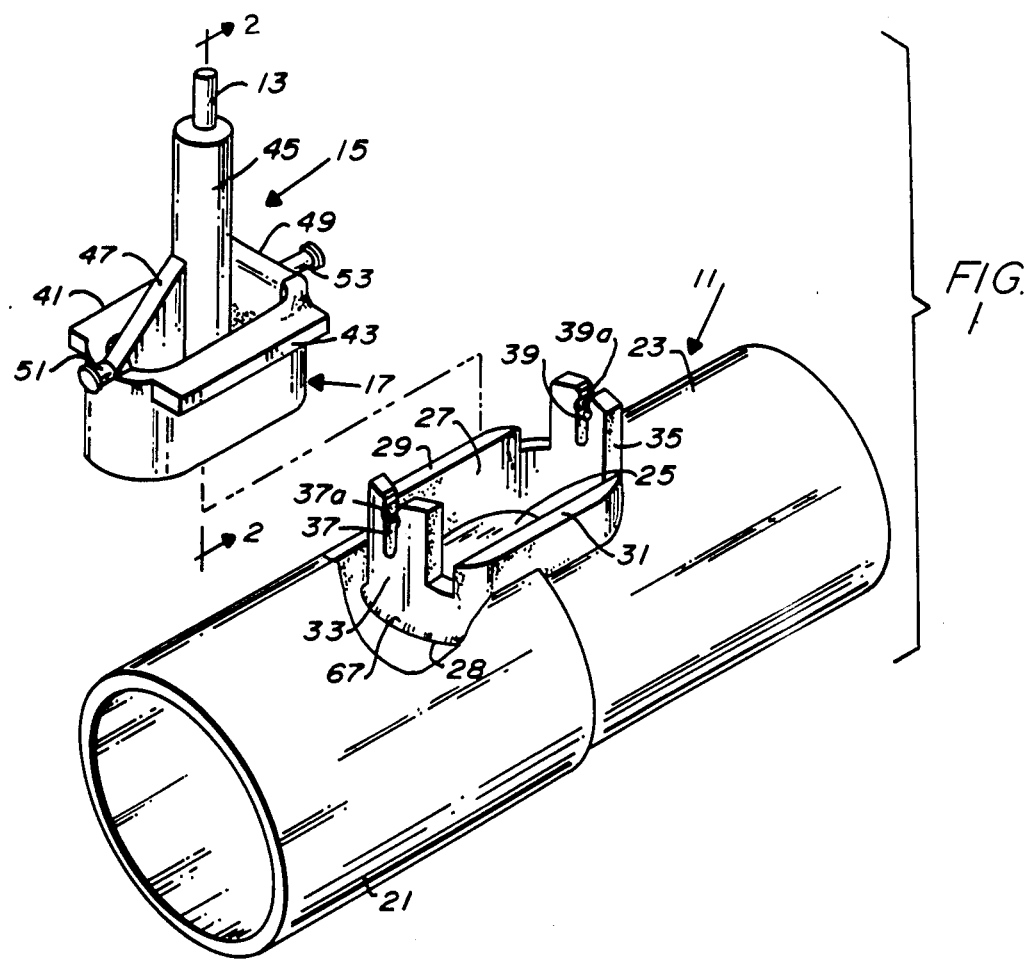
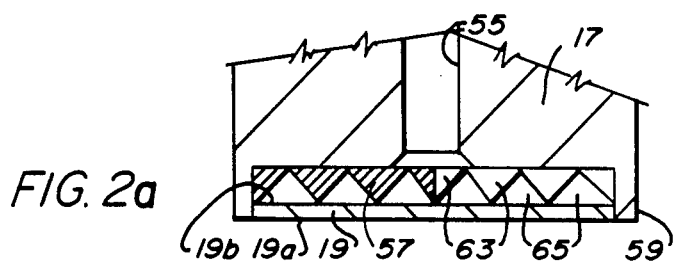
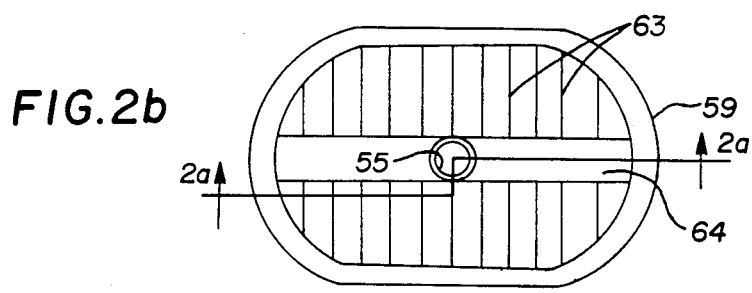

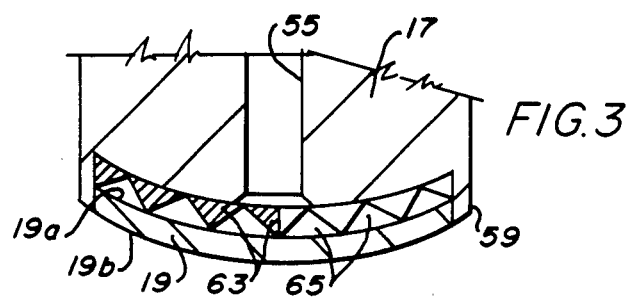
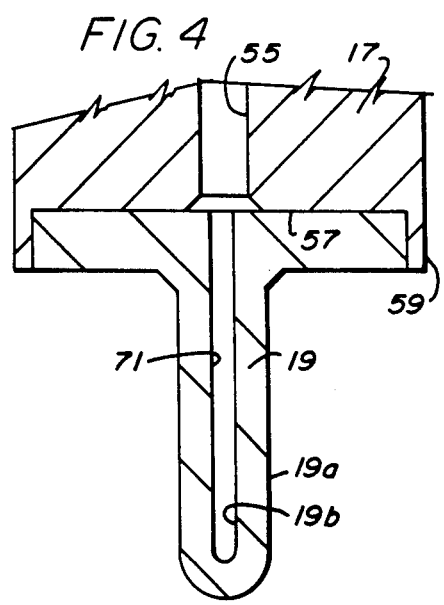

ADAPTOR ASSEMBLY FOR AIRWAY TUBE

This is a continuation of application Ser. No. 670,308, filed Nov. 8, 1984, now abandoned.

This invention relates generally to the sampling of gas in an airway tube attached to a patient. More particularly, the invention relates to an adaptor assembly for conducting sample breath gas from the airway tube to a breath gas analyzer or the like.

The analysis of breath gas or other airway gases of patients under hospital care can provide significant and useful information to attending physicians. Such monitoring may be employed where the patient is under anesthesia, or where a patient is on a respirator or similar life support system. An example of such analyzing methods and apparatus may be found in U.S. Pat. No. 4,423,739, assigned to the assignee of the present invention.

Apparatus of the foregoing type is typically coupled to the patient's airway through a sampling catheter or sample tube. This tube typically consists of about three to eight feet of very small inside diameter tubing (e.g. 0.040 inch diameter). Although a simple T-type connection to the patient's airway or breathing tube is possible, saliva and other exhaled liquids or solids, frequently present in the airway or breathing tube of the patient, may clog the inlet to the relatively small diameter sample tube.

To avoid clogging of the sample tube, various expedients have been employed to prevent interference with the operation of gas analyzers attached to the sample tube. Once such expedient is the placement of a water trap to accumulate moisture laden patient exhalations. Other expedients known in the prior art include various types of filter arrangements employed at the airway tube end of the sample tube leading to the gas analyzer device.

A major problem with prior art attempts to exclude moisture, liquids, and the like from the analyzer sample tube is that the greater the volume added to the pathway for the sample gas, the slower the response time of the analyzer. A fast response time is typically required in gas analyzers in order to accommodate respiratory rates ranging from less than 10 breaths per minute to in excess of 150 breaths per minute, which is a reasonable range to be expected. Thus, a total system response time of as low as 80 milliseconds may be required.

Accordingly, it is an object of the present invention to provide an improved adaptor assembly for sampling gas in an airway tube attached to a patient.

Another object of the invention is to provide an improved adaptor assembly which is substantially unaffected as a result of the presence of liquids and the like in the patient's airway tube.

A further object of the invention is to provide an adaptor assembly utilizing a filter probe within the patient's airway and which does not significantly add to the response time of a breath gas analyzing system connected to the filter probe.

Other objects of the invention will become apparent to those skilled in the art from the following description, taken in connection with the accompanying drawings wherein:

FIG. 1 is an exploded view, with part broken away, of an adaptor assembly constructed in accordance with the invention;

FIG. 2(a) is an offset cross-sectional view of a portion of the apparatus of FIG. 1, taken along the line 2—2 of FIG. 1;

FIG. 2(b) is plan view of filter probe 17 from the bottom with the filter removed;

FIG. 3 is a cross-sectional view similar to FIG. 2 illustrating an alternate embodiment of the invention; and FIG. 4 is cross-sectional view analogous to those of FIGS. 2 and 3 illustrating a further embodiment of the invention.

Very generally, the adaptor assembly of the invention comprises a tubular section 11 adapted to be secured in series with the patient's airway tube, not illustrated. A sample tube 13, not part of the claimed structure, leads to the gas analyzing apparatus, not shown, and is secured by a mounting subassembly 15 in communication with the tubular section 11 intermediate the ends thereof. The subassembly includes a filter probe 17 extending transversely of the axis of the tubular section a predetermined distance across the interior thereof to provide filtered communication between the interior of the tubular section and the sample tube. The filter probe includes a filter 19 having an exposed filter surface area sufficient to allow a predetermined flow rate of gas from the tubular section to the sample tube and has a ratio of exposed filter surface area to void volume within the subassembly in excess of about 10 to 1 in square centimeters to cubic centimeters. The filter probe has a porosity which is high enough to permit a predetermined flow rate of gas from the tubular section to the sample tube, but which is low enough to exclude liquid and solid matter sufficient to clog the sample tube.

Referring now in greater detail to FIG. 1, the tubular section 11 may be of any suitable construction so as to be insertable in series in the airway or breathing tube attached to the patient. In the illustrated embodiment, the tubular section 11 is formed of a suitable plastic material or the like and includes two axially aligned contiguous cylindrical sections 21 and 23. The section 21 is of slightly larger diameter than the section 23, both externally and internally. The upstream end of the airway tube, not illustrated, that is, the end which leads to the patient, fits within the cylindrical section 21. The downstream portion of the breathing tube fits over the outside of the cylindrical section 23. Within the tubular section 11, with the airway tube inserted in the cylindrical section 21, the internal diameter of the tubular section 11 is substantially uniform, except for the probe 17 as described below. The configuration and dimensions of the tubular section 11 are preferably such as to be compatible with standard tubes and fittings used in hospital applications.

A generally oval opening 25 is provided in the tubular section 11 extending across the juncture between the two cylindrical sections 21 and 23. The opening 25 is surrounded by a correspondingly oval wall 27 which may be molded integrally with the remainder of the tubular section 11 and which projects into its interior terminating at a uniform lower edge 28 approximately half-way across the interior of the tubular section. The upper surface of the wall 27 is of an irregular configuration, providing two elongated upper surfaces 29 and 31 on opposite sides of the opening 25. At the extreme ends of the oval opening 25, the wall 27 is provided with two sections 33 and 35 which extend from the tubular section 11 farther than the portions of the wall 27 upon which the surfaces 29 and 31 are provided. These wall sections 33 and 35 are each provided with a keyway 37 and 39 therein, each keyway being provided with a detent section 37a and 39a, respectively.

A sample tube mounting subassembly 15 is secured in the opening 25 and is shown in exploded position in FIG. 1. The subassembly 15 includes a filter probe portion 17 which mates with and extends through the opening 25. The distance which the filter probe 17 projects into the interior of the tubular section 11 is equal to the distance the lower edge 28 of the wall 27 projects, and is controlled by a pair of shelves 41 and 43 which extend on opposite sides of the subassembly 15. These shelves rest upon the surfaces 29 and 31 when the subassembly 15 is inserted into position. Thus the shelves 41 and 43 serve as locators for the subassembly.

Projecting upwardly from the filter probe 17 and forming part of the subassembly 15 is a sample tube attachment cylinder 45. The cylinder is buttressed by a pair of triangular buttresses 47 and 49 on opposite sides and contains an interior passage 55, not shown in FIG. 1, which extends axially of the cylinder and communicates with the lower end of the filter probe 17, as will be discussed in greater detail in connection with FIG. 2. The sample tube 13 inserts into the passage 55. Projecting from the subassembly 15 at opposite ends thereof are two cylindrical keys 51 and 53. These keys slide into the keyways 37 and 39, respectively, and are locked in the detents 37a and 39a, respectively, due to the resilience of the material of which the walls 33 and 35 are comprised. The net result of this arrangement is a convenient and easy to use snap fit for the subassembly 15, enabling it to be readily replaced as needed.

Around the lower outer periphery of the oval shaped wall 27, there is provided an annular dam 67. The dam 67, extends around the periphery of the oval wall 27 and is for the purpose of preventing liquid accumulating on the outer surface of the wall 27 from migrating to the surface of the filter itself.

The details of the filter probe 17 may be more readily observed from FIG. 2(a) and FIG. 2(b). The axial passage in the cylinder 45 extends downwardly through the filter probe 17 and is shown at 55 in FIG. 2. A recess 57 is formed in the lower surface of the filter probe 17, leaving the recess surrounded by a generally oval wall 59. The passage 55 communicates with this recess. The filter 19 spans the recess and is suitably welded or otherwise attached to the oval wall 59 at its periphery. The filter 19 includes an exterior surface 19a and an interior surface 19b. A plurality of ribs of triangular cross-section are arranged in the recess 57. These ribs, indicated at 63, are arranged so as to leave a space 64 extending transversely of the recess 57 extending across the recess in the center thereof where the passage 55 terminates. The net result is to form a plurality of longitudinal passages 65 adjacent the side 19b of the filter 19. The size and configuration of the ribs 63 are selected so as to result in a predetermined total void volume in the subassembly 15 as will be described below.

The void volume provided by the subassembly 15 is selected so as to provide as small a level of void volume as possible. The void volume is made up of the passages 65, the transverse space 64 spanning the recess 57 at the termination of the passage 55, and the passage 55 itself into which the sample tube 13 is inserted at the opposite end of the cylinder 45 from the filter probe 17. This void volume is preferably less than 0.05 cubic centimeters including the void volume added as a result of voids in the filter 19 itself.

The filter material selected may be of any suitable type. For example, self-supporting sintered porous plastic, and woven or non-woven fibrous materials, including plastics and glass are suitable. The pore size is selected to exclude what is desired and represents a compromise between flow rate and exclusionary capability. Hydrophobic materials such as polyethylene and polypropylene, and various fluorocarbon materials, are of advantage due to their moisture shedding qualities. Typically, a pore size of about 100 microns will exclude large globules, but if microbial exclusion is desired, a substantially smaller pore size is required.

The surface area of the filter should be sufficient to ensure passage of adequate breath gas for analysis in spite of the presence of occluding liquid or solid materials on the surface of the filter. This may vary from application to application but is preferably of the order of one square centimeter or larger. It is preferred that the ratio of the surface area of the filter to the dead volume of the sample tube mounting subassembly be at least about 10 to 1 square centimeters to cubic centimeters. A preferred range is from about 12 to about 20.

Referring to FIG. 3, an alternate configuration for the filter probe 17 is illustrated. In the embodiment of FIG. 3, the general shape of the lower surface of the filter probe, namely the recess 57 and the filter 19, is made dome shaped. In this way there may be less of a tendency for liquid to accumulate on the surface of the filter 19.

Referring now to FIG. 4, a further embodiment of the invention is illustrated. In FIG. 4, the filter 19 is self supporting, rather than being supported by a plurality of ribs such as the ribs 63 in FIGS. 2 and 3. The filter material is formed in the shape of a cylindrical finger which protrudes into the tubular section 11 and which is provided with a central bore 71 in the filter which extends to the passage 55 in the filter probe 17. In the particular embodiment illustrated in FIG. 4, the void volume in the filter is made up of the filter's own porosity, its central passage 71, and the added void volume of the passage 55.

With respect to all of the preceding described embodiments, it is preferred to minimize the percent which the filter probe obstructs the patient's airway, namely, the interior of the tubular section or sample tube 13. The projection must be sufficient so as to avoid migration of fluids accumulating along the walls of the tube to the filter itself. It is preferred that the filter probe obstruct less than about 40% of the cross-sectional area of the tubular section.

It will be apparent to those skilled in the art that the foregoing described invention constitutes an adaptor assembly in which the dead volume that the adaptor assembly adds to the total dead volume of the sampling system is minimized. This is accomplished by minimal obstruction to the patient's airway while providing a substantial ratio of filter surface area to dead volume to maximize the exclusion of mucus, secretions and droplets of water, as well as other substances which are typically present in the airway of a patient and which could result in occlusion of the sample line.

Various modifications of the invention will be apparent to those skilled in the art from the foregoing description and accompanying drawings. Such modifications are intended to fall within the scope of the appended claims.

What is claimed is:

1. An adaptor assembly for sampling gas in an airway tube attached to a patient, said adaptor assembly comprising, a tubular section adapted for securing in series with the airway tube, said tubular section having an opening between the opposite ends thereof, sample tube connecting means for securing a sample tube in communication with the interior of said tubular section intermediate the ends thereof, said connecting means being secured to said tubular section at said opening therein and including a filter probe extending a predetermined distance across the interior of said tubular section to provide filtered communication between the interior of said tubular section and said sample tube, said filter probe having a filter at the end thereof inside said tubular section, said filter having a first filter surface area exposed to the interior of said tubular section and a second surface area opposite said first surface area, means defining a void volume contiguous with said second surface area, said first surface area having a ratio of surface area to void volume in excess of 10 to 1 square centimeters to cubic centimeters.

2. An adaptor assembly according to claim 1 wherein said void volume defining means include means for supporting said filter by engaging said second surface area.

3. An adaptor assembly according to claim 2 wherein said supporting means include a plurality of substantially parallel ribs.

4. An adaptor assembly according to claim 1 wherein said filter probe extends a substantial distance across the interior of said tubular section.

5. An adaptor assembly according to claim 1 wherein said filter is substantially planar and has an outer surface exposed to the interior of said tubular section and an inner surface, and wherein said filter probe includes a plurality of channels immediately adjacent said inner surface of said filter and providing passages from said filter to the sample tube.

6. An adaptor assembly according to claim 1 wherein said filter probe is a size such as to obstruct less than about 40% of the cross-sectional area of the interior of said tubular section.

7. An adaptor assembly for sampling gas in an airway tube attached to a patient, said adaptor assembly comprising, a tubular section adapted for securing in series with an airway tube, said tubular section comprising a substantially cylindrical wall having a longitudinal axis and an opening in said wall between the opposite ends thereof, a sample tube mounting subassembly having attachment means for securing a sample tube in communication with said tubular section intermediate the ends thereof, said subassembly being mounted to said tubular section at said opening in said wall thereof and including a filter probe extending transversely of said longitudinal axis of said cylindrical wall a predetermined distance across the interior of said tubular section to provide filtered communication between the interior of said tubular section and said sample tube, said filter probe having a filter at the end thereof inside said tubular section with a first filter surface area exposed to the interior of said tubular section, said filter probe having a recess therein coextensive with said filter, said recess having means therein comprising a plurality of ribs for supporting said filter spaced from the bottom of said recess to leave a void volume therein, said filter probe further having a passage therein communicating between said void volume in said recess and said sample tube, said first and opposite surfaces being substantially equal in area, said void volume in said recess combined with the void volume in said passage being selected to have a ratio of filter first surface area to void volume in excess of about 10 to 1 square centimeters to cubic centimeters.

8. An adaptor assembly for sampling gas in an airway tube attached to a patient, said adaptor assembly comprising, a tubular section adapted for being secured in series with the airway tube, said tubular section having an opening between the opposite ends thereof, sample tube connecting means for securing a sample tube in communication with the interior of said tubular section intermediate the ends thereof, said connecting means being secured to said tubular section at an opening therein and including a filter probe positioned to provide filtered communication between the interior of said tubular section and said sample tube, said filter probe having a filter positioned to communicate with the inside of said tubular section, said filter comprising first and second substantially parallel planar surfaces and a plurality of filter pores connecting said first and second surfaces, said first surface being exposed to the interior of said tubular section, said filter probe further comprising a recess contiguous with said second surface of said filter and a conduit for connecting said recess to said sample tube, said recess having a plurality of ribs therein in contact with said second filter surface for supporting said filter, said ribs being oriented and spaced from each other to define a plurality of passageways in communication between said second surface and said conduit, said passageways and the said filter pores defining a void volume, the ratio of the surface area of said first filter surface to said void volume being greater than 10 to 1 square centimeters to cubic centimeters.

* * * * *